US00PP22632P2

(12) United States Plant Patent
Olesen

(10) Patent No.: US PP22,632 P2
(45) Date of Patent: Apr. 10, 2012

(54) GROUNDCOVER ROSE PLANT NAMED 'POULTC015'

(50) Latin Name: ***Rosa* hybrid**
Varietal Denomination: Poultc015

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 12/930,443

(22) Filed: Jan. 7, 2011

(51) Int. Cl.
*A01H 5/00* (2006.01)

(52) U.S. Cl. ..... Plt./105; Plt./102

(58) Field of Classification Search ..... Plt./105, Plt./102, 101
See application file for complete search history.

*Primary Examiner* — Kent L Bell

(57) ABSTRACT

A new garden rose plant of the ground cover class which has abundant, orange blend flowers and attractive foliage. This new and distinct variety has shown to be uniform and stable in the resulting generations from asexual propagation.

2 Drawing Sheets

Botanical designation: *Rosa* hybrid.
Variety denomination: 'Poultc015'.

SUMMARY OF THE INVENTION

The present invention constitutes a new and distinct variety of garden rose plant which originated from a controlled crossing between the female seed parent, an unnamed, non-commercial seedling, and the male pollen parent, also an unnamed, non-commercial seedling.

The two parents were crossed during the summer of 2001 and the resulting seeds were planted in a controlled environment in Fredensborg, Denmark. The new variety, named 'Poultc015', originated as a single seedling from the stated cross.

The new variety may be distinguished from its female seed parent by flower color. The seed parent has yellow flowers while the new variety has yellow-orange flowers.

The new variety may be distinguished from its male pollen parent by the following combination of characteristics. The pollen parent is more upright and taller in growth habit than 'Poultc015'.

The objective of the hybridization of this rose variety was to create a new and distinct variety for garden use with unique qualities, such as:

1. Uniform and abundant orange blend flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poultc015' from all other varieties of which we are aware.

As part of the rose development program, Mogens N. Olesen germinated the seeds from the aforementioned hybridization during winter of 2001 and conducted evaluations on the resulting seedlings in a controlled environment in Fredensborg, Denmark. 'Poultc015' was selected in the spring of 2002 by the inventor as a single plant from the progeny of the aforementioned hybridization.

Asexual reproduction of 'Poultc015' by traditional budding and rooted cuttings was first done by Mogens N. Olesen in the nursery in Fredensborg, Denmark in July, 2002. This initial and other subsequent asexual propagations conducted in controlled environments have demonstrated that the characteristics of 'Poultc015' are true to type and are transmitted from one generation to the next.

BRIEF DESCRIPTION OF THE DRAWING

The accompanying color illustrations show as true as is reasonably possible to obtain in color photographs of this type, the typical characteristics of the buds, flowers, leaves, and stems, of 'Poultc015'. Specifically illustrated in the drawings are.

DETAILED DESCRIPTION OF THE VARIETY

Figure 1:
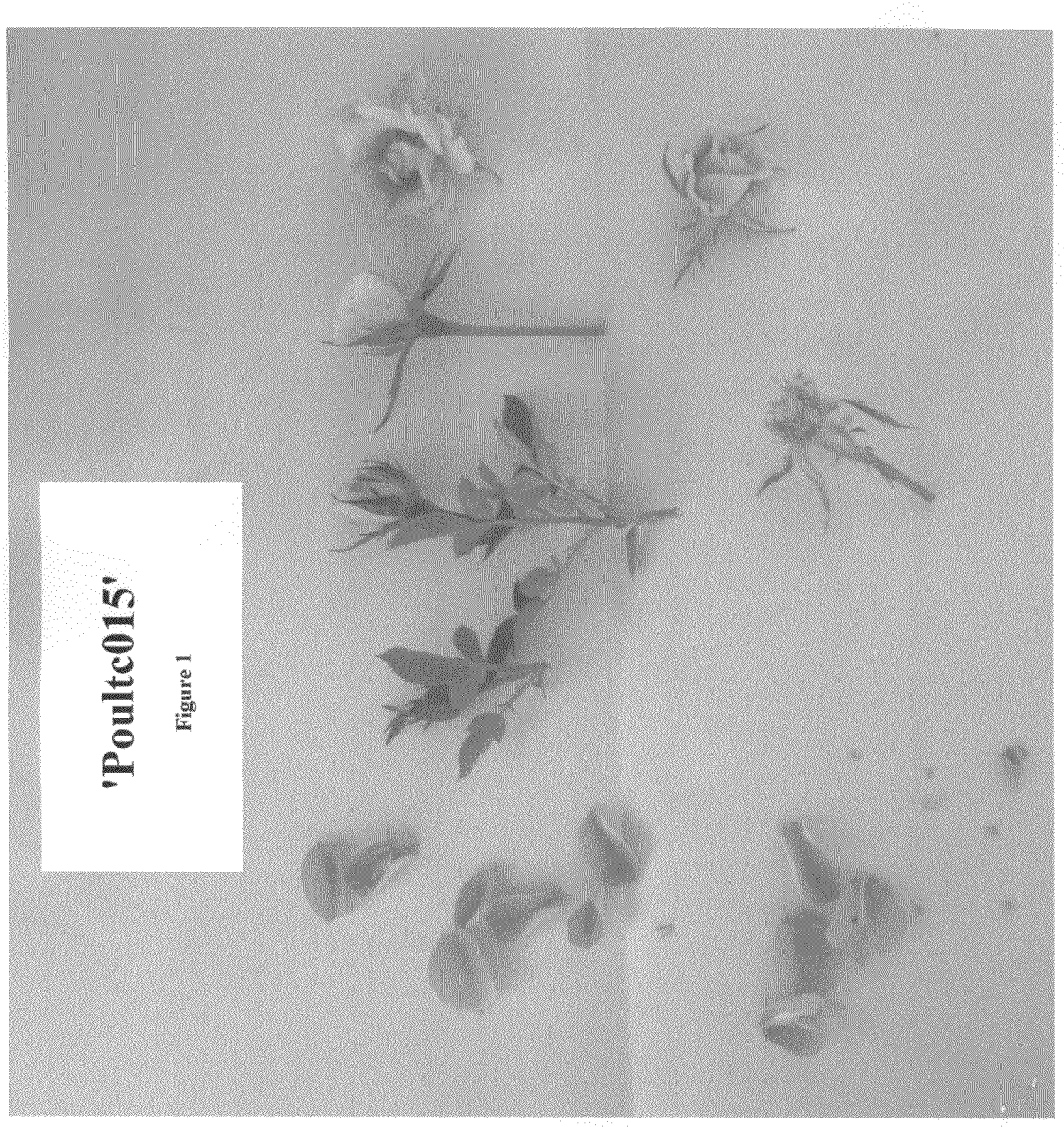
FIG. 1: Open flowers, flower petals detached, and reproductive parts.
Figure 2:
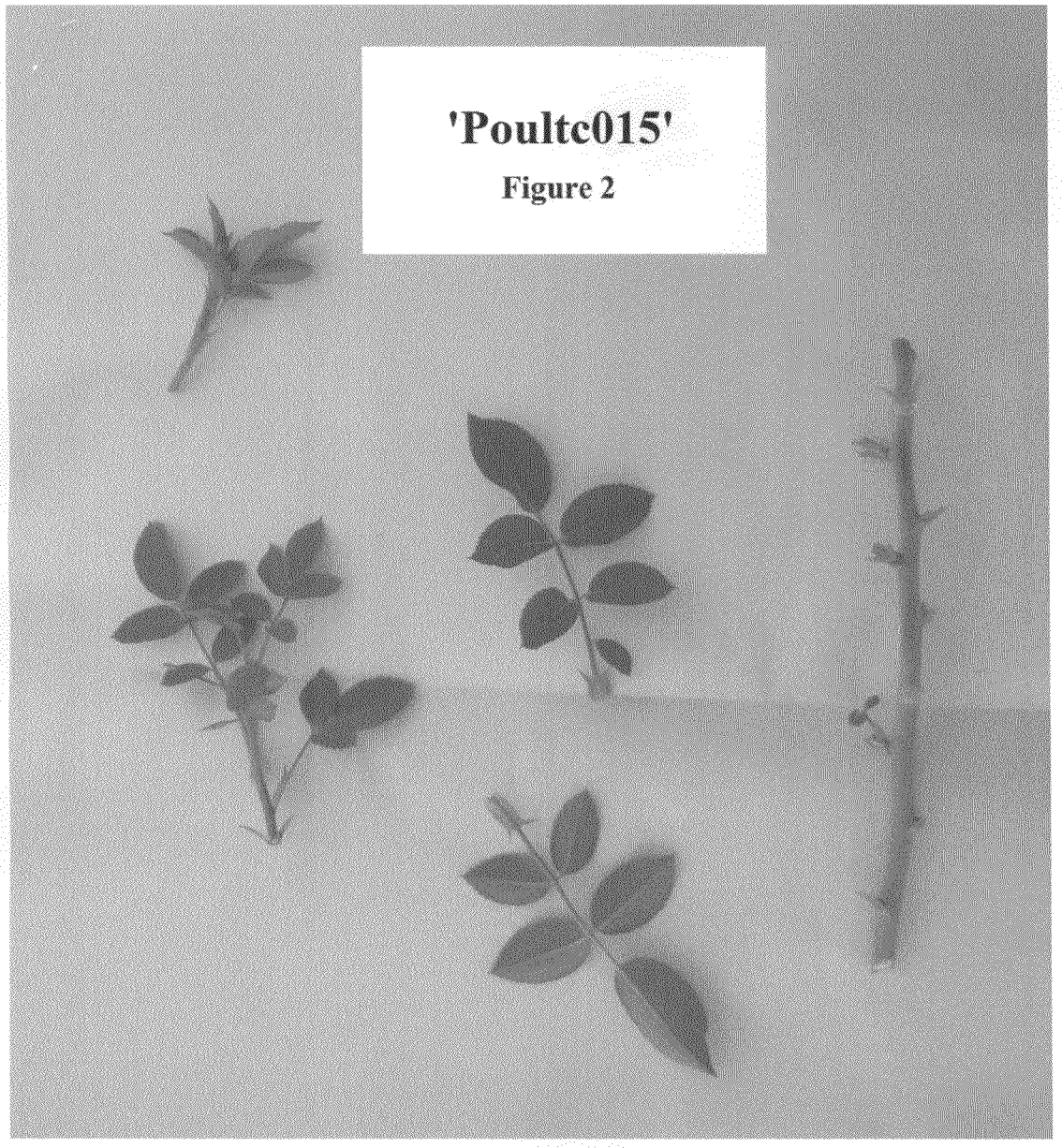
FIG. 2: Juvenile growth, mature leaves, and bare stem.

The following is a description of 'Poultc015', as observed in its growth in a field nursery in Jackson County, Oreg. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poultc014', U.S. Plant Pat. No. 18,444, are compared to 'Poultc015' in Chart 1.

CHART 1

| | 'Poultc015' | 'Poultc014' |
|---|---|---|
| Petal Count | 20 | 35 |
| Flower Diameter | 50 to 60 mm | 30 mm |
| General Tonality of Flower Color | On open flower Orange Group 24B with intonations of Orange Group 25A. Afterwards, general tonality is Yellow-Orange Group 19B with intonations of Orange Group 24B. | Yellow Group 8A to Yellow Group 10B. No change in tonality at the end of the 7th day. Afterwards, general tonality is Yellow Group 10C to Yellow Group 10D. |

FLOWER AND FLOWER BUD

Blooming habit: Continuous.

Flower bud:

*Size*.—Upon opening, 20 mm in length from base of receptacle to end of bud. Bud diameter is 10 mm.

*Bud form*.—Ovoid.

*Bud color*.—As sepals unfold, petals are Yellow-Orange Group 23C.

*Sepal inner surface*.—Color: Green Group 138B. Surface: Medium pubescence observed.

*Sepal outer surface*.—Color: Yellow-Green Group 146A. Anthocyanic pigments the color of Greyed-Purple Group 183B observed. Texture: Smooth.

*Sepal shape*.—Typically lanceolate. Broad at the base and mid-point, becoming narrow and acuminate at the apex. Base: Flat at union with receptacle.

*Sepal margin*.—Margins have strong foliaceous appendages on three of the five sepals.

*Sepal size*.—25 to 30 mm long by 7 mm wide.

*Receptacle*.—Texture: Smooth. Shape: Funnel shaped. Size: 5 mm tall by 6 mm wide on average. Color: Yellow-Green Group 146C. Anthocyanic pigments the color of Greyed-Red Group 180B observed.

*Peduncle*.—Length: 5 cm on average. Diameter: 2 to 3 mm. Color: Yellow-Green Group 145A.

*Pedicel*.—Surface: Smooth. Length: 40 mm on average. Diameter: 2 mm on average. Color: Yellow-Green Group 145A. Anthocyanic pigments the color of Greyed-Red Group 178C observed. Strength: Moderate.

Flower bud development: Flower buds are borne in clusters of 5 to 7 flower buds per stem.

Flower bloom:

*Fragrance*.—Moderate perfume, floral scent.

*Duration*.—The blooms have a duration on the plant of approximately 7 to 10 days. Petals fall cleanly away from plant after flowers have fully matured.

*Size*.—Flower diameter is 50 to 60 mm when open. Flower depth is 13 mm.

*Flower shape*.—Generally flowers are open, with 2 or 3 whorls of petals slightly overlapping.

*Shape of flower, side view*.—After opening the upper and lower portions are flattened convex.

Petalage: Under normal conditions, flowers have 20 petals total, 5 of which are petaloids.

Petal color:

*Upon opening, outer and inner petals*.—Upper surface: Orange Group 24B with shaded intonations of Yellow-Orange Group 17D. Lower surface: Yellow-Orange Group 18A with shades of Yellow-Orange Group 16B at the margins. Occasional streaks of Red-Purple Group 58B.

*Basal petal spots, upon opening*.—Upper surface: Yellow-Green Group 12A. Lower surface: Yellow-Green Group 11A.

*After opening, outer and inner petals*.—Upper surface: Yellow-Orange Group 22B with intonations of Yellow-Green Group 14A. Lower surface: Yellow-Orange Group 14C with shades of Yellow-Orange Group 16B. Occasional streaks of Red-Purple Group 58B.

*Basal petal spots, after opening*.—Upper surface: Yellow-Green Group 12A. Lower surface: Yellow-Green Group 11A.

General tonality: On open flower Orange Group 24B with intonations of Orange Group 25A. Afterwards, general tonality is Yellow-Orange Group 19B with intonations of Orange Group 24B.

Petals:

*Petal reflex*.—Weak petal reflex.

*Margin*.—Entire and uniform.

*Shape*.—Narrow elliptic. Apex shape: Cuspidate. Base shape: Acute.

*Size*.—Outer petals are 22 mm (l)×21 mm (w). Inner petals are 20 mm (l)×11 mm (w).

*Texture*.—Smooth.

*Thickness*.—Average.

Petaloids:

*Quantity*.—5 on average.

*Shape*.—Irregular and asymmetric. Occasionally there is a cleft at the margin. Apex and base are generally acute.

*Color*.—Upper surface is Orange Group 24B with shaded intonations of Yellow-Orange Group 17D. Basal petals spots are Yellow-Green Group 12A. Lower surface is Yellow-Orange Group 18A with shades of Yellow-Orange Group 16B at the margins. Occasional streaks of Red-Purple Group 58B. Basal petal spots on lower surface are Yellow-Green Group 11A.

*Size*.—20 mm (l)×7 mm (w) on Average.

Reproductive organs:

*Pollen*.—None observed.

*Anthers*.—Size: 3 mm in length. Color: Yellow Group 11B. Quantity: 100 on average.

*Filaments*.—Color: Yellow-Orange Group 14B. Length: 6 mm.

*Pistils*.—Length: 5 mm. Quantity: 50 on average.

*Stigmas*.—Level in location relative to the length of the filaments and the height of the anthers. Color: Greyed-Green Group 193C.

*Styles*.—Color: Greyed-Green Group 193C.

*Hips*.—None Observed in the field nursery in Jackson County Oreg.

PLANT

Plant growth: Bushy, well branched. When grown as a budded field grown plant on *Rosa multiflora* understock, the average height of the plant is 80 cm and the average width is 80 cm.

Stems:

*Color*.—Juvenile growth: Yellow-Green Group 144B. Mature growth: Yellow-Green Group 144B.

*Length*.—On average, canes are 20 cm from the base of the plant to the flowering portion.

*Diameter*.—5 mm.

*Internodes*.—On mature canes, there is an average distance of 30 mm between nodes.

*Surface texture*.—Young wood: Smooth. Older wood: Smooth.

Prickles:

*Incidence*.—3 prickles per 10 cm of stem.

*Size*.—Average length of prickles on mature stems is 2 mm.

*Shape*.—Concave on upper and lower surface.

*Color*.—Juvenile prickles: Yellow-White Group 158B. Mature prickles: Yellow-White Group 158B.

Plant foliage: Normal number of leaflets leaves in middle of the stem: 5 leaflets.

*Compound leaf.*—80 mm (l)×55 (w) on average.

*Quantity.*—3 leaves per 10 cm of stem on average.

*Color of mature foliage.*—Upper side: Yellow-Green Group 147A. Lower side: Yellow-Green Group 147B.

*Color of juvenile foliage.*—Upper side: Green Group 143B. Lower side: Yellow-Green Group 144B. Margins: Anthocyanic pigments the color of Greyed-Purple Group 183C.

Plant leaves and leaflets:

*Stipules.*—Size: 15 mm in length. Quantity: 2 per compound leaf. Shape: Linear, slightly broad based with outward extending apices. Margins: Finely serrated with few stipitate glands. Color: Yellow-Green Group 144A.

*Petiole.*—Length: 25 mm average. Diameter: 2 mm.

*Upper surface.*—Color: Yellow-Green Group 144A. Observations: Few stipitate glands observed.

*Lower surface.*—Color: Yellow-Green Group 144C. Texture: Smooth.

*Rachis.*—Length: 40 mm average. Diameter: 2 mm.

*Upper surface.*—Color: Yellow-Green Group 144A. Observations: Few stipitate glands observed.

*Lower surface.*—Color: Yellow-Green Group 144C. Texture: Smooth.

*Leaflet.*—Edge: Serrated. Size: Average size of the terminal leaflet on normal leaves is 31 mm in length by 24 mm wide. Shape: Generally elliptical. Base: Rounded. Apex: Mucronate. Texture: Smooth. // Rough. Thickness: Average. Arrangement: Odd pinnate. Venation: Reticulate. Glossiness: Matte, no leaf gloss.

Disease resistance: Above average resistance to powdery and downy mildew, rust, black spot, and Botrytis under normal growing conditions in Jackson County, Oreg.

Cold hardiness: The variety is tolerant to USDA Cold Hardiness Zone 6.

Heat tolerance: The variety has been found to be suitable for climate conditions found in the American Horticulture Society heat zone 7.

What is claimed is:

1. A new and distinct variety of rose plant of the ground cover rose class named 'Poultc015', substantially as illustrated and described herein, due to its abundant orange blend flowers, disease resistance, and extended period of bloom.

* * * * *

'Poultc015'

'Poultc015'